United States Patent [19]

Glatzhofer

[11] 4,387,053

[45] Jun. 7, 1983

[54] STABILIZATION OF OXIME CARBAMATES WITH GALLIC ACID, LOWER ALKYL ESTER DERIVATIVES THEREOF

[75] Inventor: James P. Glatzhofer, Chardon, Ohio

[73] Assignee: Diamond Shamrock Corporation, Dallas, Tex.

[21] Appl. No.: 323,825

[22] Filed: Nov. 23, 1981

[51] Int. Cl.³ .................. C07C 117/00; C07C 131/00
[52] U.S. Cl. ......................... 260/349; 564/2; 564/255; 252/404; 260/454; 260/465.4
[58] Field of Search ..................... 564/2, 255; 260/349

[56] References Cited

U.S. PATENT DOCUMENTS 3,875,232  4/1975  Magee .................................. 564/255

FOREIGN PATENT DOCUMENTS 2000031A  1/1979  United Kingdom .

OTHER PUBLICATIONS

CA. 95, 182281j, Thermostability Improvement of carbamate pesticides, Mitsubishi Chem. Ind. Co., Ltd. (Jpn. Kokai Tokkyo Koho 81/92,802—published 7/27/81).

Primary Examiner—Natalie Trousof
Assistant Examiner—L. Hendriksen
Attorney, Agent, or Firm—Helen P. Brush

[57] ABSTRACT

Stabilized pesticide compositions for use particularly as insecticides comprise gallic acid or the propyl ester thereof in combination with an oxime carbamate of the formula

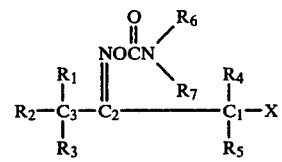

wherein $R_1$ can be $R_2$–$R_4$ or X; $R_2$–$R_4$ can be H, lower alkyl, lower alkenyl, lower alkynyl, substituted alkyl, alkenyl or alkynyl with the proviso that $R_2$ and $R_3$ may be connected to form a cycloaliphatic ring;

$R_5$ can be $R_2$–$R_4$ or X with the proviso that when $R_5$ and X are $OR_8$, $SR_8$, $S(O)R_8$, $SO_2R_8$, or $NR_8R_9$, $R_5$ and X may be connected to form a heterocyclic ring;

$R_6$–$R_7$ can be hydrogen, lower alkyl, lower alkenyl or lower alkynyl;

X = $SR_8$, $S(O)R_8$, $SO_2R_8$, $OR_8$, $OSO_2R_8$, $NR_8R_9$, $NO_2$, CN, SCN, $N_3$ or halogen; and $R_8$ = H, lower alkyl, lower alkenyl lower alkynyl, aryl or substituted aryl, carbamyl, substituted carbamyl, acyl, or substituted acyl; and $R_9$ = H or lower alkyl with the proviso that $R_8$, $R_9$ and N in the $NR_8R_9$ group may form a heterocyclic ring.

8 Claims, 1 Drawing Figure

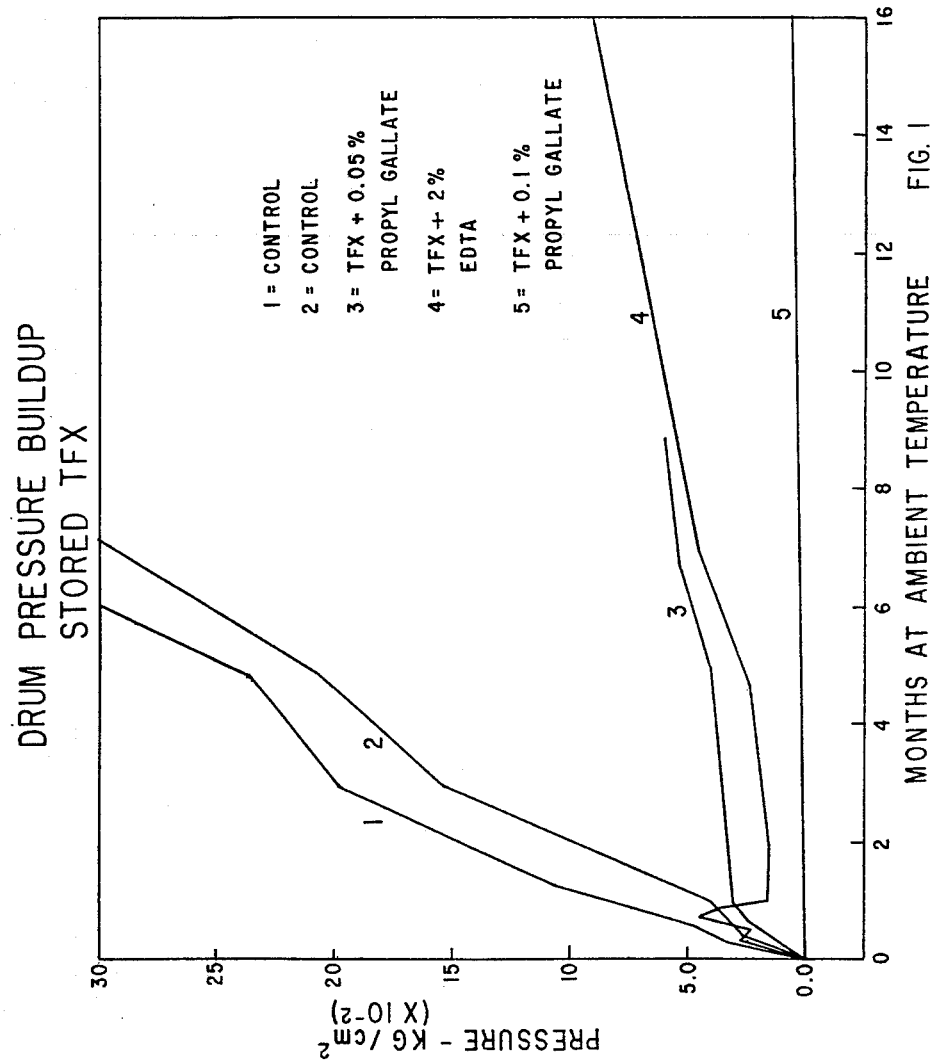

STABILIZATION OF OXIME CARBAMATES WITH GALLIC ACID, LOWER ALKYL ESTER DERIVATIVES THEREOF

BACKGROUND OF THE INVENTION (1) Field of the Invention

This invention relates to organic compounds useful as pesticides. More particularly, it is directed to thermally stabilized carbamate derivatives of oximes having commercial importance as miticides, as nematocides, and especially as insecticides, and to the process for preparing these stabilized compositions.

(2) Description of the Prior Art

An oxime carbamate derivative such as 3,3-dimethyl-2-methylcarbamyloximino-1-methylthiobutane, commonly known as thiofanox (or TFX) has enjoyed increasing success as an effective insecticide. It typically is formuated for commercial application into granular products containing 5, 10 or 15 percent of the oxime carbamate as active ingredient. These products are prepared by impregnating inert granular carrier materials such as Fuller's earth and other clay-like, highly absorptive mineral mixtures, with the oxime carbamate. However, as the chemical is a solid at room temperature, it must be melted prior to application onto the carrier. It becomes highly unstable with warming, oftentimes decomposing significantly.

British patent application No. 2,000,031, published Jan. 4, 1979, in the name of Shell Internationale Research Maatschappij B.V., teaches the use of ethylenediaminetetraacetic acid (EDTA) and/or an alkali metal salt thereof as stabilizer for technical-grade oxime carbamates, said EDTA acid or salt serving to prevent substantial decomposition of the technical-grade materials during warming and formulating. EDTA and/or the alkali metal salt thereof, being only slightly soluble in water, are likewise substantially insoluble in technical-grade oxime carbamate. Thus, they must be slurried into the molten chemical and may settle out to a significant degree when the molten carbamate slowly cools and solidifies. As taught by the aforesaid patent application, generally from 0.5 to 5.0 molar percent and preferably, from 1.0 to 2.0 molar percent of EDTA-containing materials are employed in order to suppress the significant decomposition of said carbamate with warming and formulating.

It has now been found that use of compounds other than EDTA provide equivalent, if not improved stability to technical-grade oxime carbamates during melting thereof, while providing other formulating advantages thereto.

SUMMARY OF THE INVENTION

Accordingly, the present invention provides pesticide compositions which are stable to decomposition during formulation and/or in storage which compositions comprise gallic acid and/or a lower alkyl ester thereof in combination with an oxime carbamate of the general structural formula

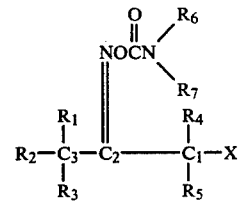

wherein $R_1$ can be $R_2$–$R_4$ or X; $R_2$–$R_4$ can be H, lower alkyl, lower alkenyl, lower alkynyl, substituted alkyl, alkenyl or alkynyl with the proviso that $R_2$ and $R_3$ may be connected to form a cycloaliphatic ring;

$R_5$ can be $R_2$–$R_4$ or X with the proviso that when $R_5$ and X are $OR_8$l, $SR_8$, $S(O)R_8$, $SO_2R_8$, or $NR_8R_9$, $R_5$ and X may be connected to form a heterocyclic ring;

$R_6$–$R_7$ can be hydrogen, lower alkyl, lower alkenyl or lower alkynyl;

$X = SR_8$, $S(O)R_8$, $SO_2R_8$, $OR_8$, $OSO_2R_8$, $NR_8R_9$, $NO_2$, CN, SCN, $N_3$ or halogen; and $R_8 = $H, lower alkyl, lower alkenyl lower alkynyl, aryl or substituted aryl, carbamyl, substituted carbamyl, acyl, or substituted acyl; and $R_9 = $H or lower alkyl with the proviso that $R_8$, $R_9$ and N in the $NR_8R_9$ group may form a heterocyclic ring.

In particular, the oxime carbamates within the above-defined structure which are, at present, most advantageously stabilized in accordance with the present invention are represented by the structural formula:

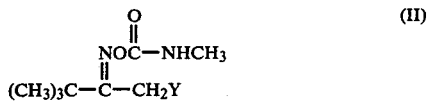

wherein Y is $—SCH_3$ or $—N_3$.

BRIEF DESCRIPTION OF THE DRAWING

The advantages of this invention will become apparent upon reading the following detailed description and upon reference to the drawing (FIG. 1) which is a graph showing the much greater decomposition rates of unstabilized TFX even at ambient temperature, compared to TFX containing either EDTA or very minor amounts of propyl gallate as thermal stabilizer therefor.

DESCRIPTION OF THE PREFERRED EMBODIMENTS

Specific carbamate compounds conforming to structure II are 3,3-dimethyl-2-methylcarbamyloximino-1-methylthiobutane; and 1-azido-3,3-dimethyl-2-methylcarbamyloximino-butane. As mentioned earlier, the first-named compound known commonly as thiofanox is, at the present time, of greater importance commercially as an excellent pesticide for controlling insects, mites and nematodes.

The oxime carbamates stabilized in accordance with this invention are described and claimed in U.S. Pat. No. 3,875,232 (Thomas A. Magee) issued Apr. 1, 1975, the disclosure of which is incorporated herein by reference. These carbamates may be satisfactorily stabilized as prepared, without further purification or other processing. Such unpurified carbamates are designated hereinafter as "technical" or "technical-grade."

The stabilizer of this invention, either gallic acid or a lower alkyl ester thereof, the propyl ester being preferred, may effectively be employed in an amount as low as 0.05 percent by weight of the composition. In general, the stabilizer may be employed in an amount ranging from 0.05 to 5.0 percent, by weight, with no deleterious effects on the carbamate composition. However, as this stabilizer provides the desired stability when employed in amounts of 0.05 to 2.00 percent and most preferably, in amounts of 0.10 to 1.00 percent, by weight of the composition, it is both unnecessary and too costly to employ the stabilizer in an amount greater than 2.00 percent by weight of the composition. It can easily be recognized that the preferred quantities of stabilizer used herein are much reduced from amounts of EDTA necessary to provide the desired stabilization to the carbamate composition.

A further advantage in using the stabilizers of this invention rather than the EDTA materials of the earlier described published British application (No. 2,000,031) is that gallic acid and its propyl ester, both of which are high melting, crystalline compounds, are soluble in the oxime carbamate materials. In practice of the invention, therefore, these solid stabilizers may simply be added to the molten chemical with stirring, quickly being dissolved homogeneously therein.

To facilitate field application of the oxime carbamate, a pesticidal composition according to this invention typically will contain a suitable solid carrier for the chemical and stabilizer. In general, this carrier may be inorganic or organic in nature, synthetic or natural in origin. Presently, an inorganic granular material such as Fuller's earth, montmorillonite and the like is the preferred solid carrier. Such carrier material inherently contain metals such as iron, magnesium, etc., which could catalyze decomposition of the carbamate active ingredient. Further, the carrier material to be employed may be treated with a "deactivator" compound prior to its impregnation with the active ingredient and stabilizer. Such deactivator compounds are believed to react with acid and/or basic reactive sites on the carrier, thus preventing these sites from later reacting with impurities in the active ingredient and accelerating its decomposition. Suitable carrier deactivators include aliphatic polyols such as dipropylene glycol and solvents such as cyclohexanone.

The pesticide compositions of this invention may be satisfactorily prepared by various methods. In one instance, propyl gallate, in solution in acetone, is impregnated onto the carrier. Thereafter, the carbamate active ingredient is impregnated onto the carrier, employing a solvent which has negligible solubility for the stabilizer, e.g., methylene chloride. In this way, the stabilizer will be maintained at the carbamate-carrier interface. Thereafter, the solvent normally is quickly removed via, e.g., a rotary evaporator. Samples of the dried, impregnated samples then are immediately extracted with a solvent such as a lower aliphatic alcohol to obtain the initial assay of the TFX technical before any decomposition of the carrier has time to occur. In another method, TFX technical is melted and the propyl gallate stabilizer is dissolved in the molten TFX prior to impregnating the carrier therewith. In still another, though less preferred method, the stabilizer and TFX may be dissolved together in an appropriate solvent, after which the resulting solution is sprayed onto the carrier. The solvent is then quickly removed.

Insects are combatted by applying an effective amount of a composition according to this invention either to the insects themselves or to their habitat. For a fuller understanding of the nature and objects of this invention, the following specific examples are given. These examples, however, are not to be construed as limiting the invention in any way.

EXAMPLE 1

Oxime Carbamate Preparation

The compound, 3,3-dimethyl-2-methylcarbamyloximino-1-methylthiobutane (thiofanox) was prepared according to the teachings of U.S. Pat. No. 3,875,232, as follows:

To a dried 100 ml. flask equipped with a condenser fitted with a drying tube were added 4.8 g. (0.03 mole) of 3,3-dimethyl-1-methylthio-2-butanone oxime, of methylisocyanate and three drops of triethylamine in 40 ml. of anhydrous ether. The resulting reaction mixture was heated at reflux for 12 hours. It was then stripped through a rotary evaporator at reduced pressure, yielding a yellow liquid which solidified to a white solid upon standing. This product was indentified as the desired 3,3-dimethyl-2-methylcarbamyloximino-1-methylthiobutane (Empirical formula $C_9H_{18}N_2O_2S$) by the following elemental analysis: Calculated=C, 49.5; H, 8.3; N, 13.0 percent; Found=C, 49.3; H, 8.9; and N, 12.9 percent.

EXAMPLE 2

To illustrate the efficiency of propyl gallate to retard the production of gaseous reaction and/or decomposition products in thiofanox technical, a 55-gallon drum of technical material was melted at <70° C. for approximately 22 hours. The molten material was then transferred to a series of pre-tared 5-gallon epoxy-phenolic lined cans, leaving approximately 5 cm. headspace. The cans were equipped with threaded bung holes 5 cm. in diameter.

The actual weight of thiofanox in each can was determined by weighing the filled cans and subtracting the tared weight of the can prior to filling. Based on these actual weights, the required amounts of propyl gallate, hammermilled to a powder ≦200 mesh, were added to the cans and shear mixed into the molten TFX with a dispersator until the stabilizer was solubilized (about five minutes). As controls, two TFX-filled cans with no added propyl gallate were similarly stirred. Also, for comparison purposes, 2 percent of powdered ethylenediamine tetraacetic acid (EDTA) was added to a can filled with molten TFX, and dispersed therein with shear mixing for about five minutes, using the dispersator. Small samples of each TFX mixture were taken and dispensed into 25×20 ml. scintillation vials (∼3 g. sample/vial) for thermal stability testing.

The sealed cans were stored for at least two days at ambient temperature to permit equilibration and complete crystallization of the TFX. A pressure gauge was then affixed to each can using a 2 cm.-5 cm. stainless steel bushing. Further, a pressure septum may be affixed to the tee-connectors of the pressure gauge set-up to permit headspace samples to be drawn as desired.

The sealed drums were then stored at ambient temperature, being monitored at least once a week and then at prescribed intervals, as shown on the table below, until completion of the test. The results obtained from this test are as follows:

TABLE 1

| Sample | 1 | 2 | 3 | 4 | 5 | 6 | 7 | 8 |
|---|---|---|---|---|---|---|---|---|
| Wt Percent, Propyl Gallate Added | 0 | 0.05 | 0.1 | 0.5 | 1.0 | 2.0 | 0 | 0 |
| Wt Percent, EDTA Acid Added | 0 | 0 | 0 | 0 | 0 | 0 | 2.0 | 0 |
| Pressure Reading | | | | Kilograms/cm$^2$ ($\times 10^{-2}$) | | | | |
| Storage Time | | | | | | | | |
| 1 day | 0 | 0 | 0 | 0 | 0 | 0 | 5.6 | 0 |
| 5 days | 0 | 4.2 | 0 | 0 | 0 | 0 | 4.9 | 0 |
| 1 week | 3.9 | 4.2 | 0 | 0 | 0 | 0 | 3.9 | 3.5 |
| 3 weeks | 3.9 | 3.9 | 0 | 0 | 0 | 0 | * | 10.5 |
| 5 weeks | 8.4 | 4.9 | 0 | 0 | 0 | 0 | * | 16.2 |
| 12 weeks | 18.3 | 3.9 | 0 | 0 | 0 | 0 | * | 24.6 |
| 17 weeks | 21.8 | 4.9 | 0 | 0 | 0 | 0 | * | 28.1 |
| 24 weeks | 25.3 | 5.6 | 0 | 0 | 0 | 0 | 4.2 | 37.3 |
| 8 months | — | 8.4 | 0 | 0 | 0 | 0 | 7.4 | — |
| 9 months | — | 8.4 | 0 | 0 | 0 | 0 | 8.4 | — |
| 11 months | — | — | 0 | 0 | 0 | 0 | 10.5 | — |
| 13 months | — | — | 0 | 0 | 0 | 0 | 10.5 | — |
| 16 months | — | — | 0 | 0 | 0 | 0 | 12.7 | — |

*Pressure below lowest scale reading, although slightly positive.

The above results illustrate that TFX sample Nos. 3, 4, 5 and 6, which contained, respectively, 0.10, 0.50, 1.0 and 2.0 percent, by weight, of propyl gallate had no pressure buildup during the entire 16 months of storage. TFX which incorporated 0.05 percent propyl gallate, by weight (Sample No. 2), did develop comparatively steady pressure over 11 months, about the same as the can which contained TFX with 2.0 percent ethylenediaminetetraacetic acid, by weight (Sample No. 7). Both TFX controls were increasingly unstable throughout the storage period.

The foregoing results are graphically illustrated in FIG. 1 wherein pressure (Kg/cm$^2$) developed in the sealed samples is plotted against months of storage at ambient temperature. The unstabilized TFX controls (Curves 1 and 2) are seen to become significantly decomposed when stored for less than 8 months, as evidenced by the steady pressure buildup in these sample containers. TFX containing 0.05 percent propyl gallate, by weight, and that containing 2 percent EDTA, by weight, appear to decompose to about the same rate as evidenced by the fairly equivalent pressure buildup shown by Curves 3 and 4 on the graph. TFX containing 0.10 percent propyl gallate, by weight (and also those with 0.50-2.0 percent thereof) shows no decomposition as indicated by zero pressure buildup in the sample containers during 16 months storage at ambient temperature (represented by Curve 5 of the graph). The pressure buildup in the EDTA-containing sample is believed to be due to the reaction of EDTA with one or more components of the technical material.

As further indication of its significant pressure buildup, sealed 55-gallon drums of the unstabilized TFX technical were stored at ambient temperature. Due to pressure developing in the headspace of the drums from decomposition of the TFX, the drum tops bulged significantly so as to constitute a potential hazard. Consequently, it was necessary to vent these drums periodically as decomposition of the active ingredient continued during storage.

EXAMPLE 3

This example illustrates the effects of various antioxidants and other additives for TFX thermal stability improvement.

For the test, a series of 20 ml. scintillation vials were weighed. Approximately 3 ml. of molten TFX technical was then pipetted into each of the vials, after which they were reweighed to provide the actual quantity of TFX contained in each vial.

Using these values, the requisite quantity of additive to be employed was weighed out and added to each vial. The TFX in each vial was melted and the additive therein was homogeneously dissolved or slurried in the TFX. Scintillation vials containing similar quantities of TFX technical solely were prepared in duplicate as controls, each sample being maintained in the molten state for approximately 3 hours.

The prepared samples were stored at 60° C. for 20 weeks, being assayed periodically during this time to determine the effectiveness of the various additives to stabilize the TFX technical compared to the decomposition rate of the controls. The initial assays of the samples were taken as 100 percent TFX technical and all subsequent assays were calculated as percentages of the initial assays. Using this procedure, results are as follows:

TABLE 2

| Sample TFX TECH. Plus | Percent TFX TECHNICAL Weeks at 60° C. | | | | | |
|---|---|---|---|---|---|---|
| | 1 | 3 | 6 | 8 | 13 | 20 |
| 2% Anh. CaSO$_4$ | 96.7 | 95.3 | 92.9 | 84.2 | 87.5 | 78.2 |
| 2% Na Thiosulfate | 94.0 | 87.7 | 80.5 | 72.9 | 74.0 | 55.9 |
| 2% BHT[1] | 97.9 | 92.3 | 85.2 | 85.1 | 83.8 | 77.4 |
| 2% EDTA Acid | 98.7 | 90.6 | 91.5 | 87.0 | 89.9 | 92.7 |
| 5% Cyclohexane | 95.0 | 92.6 | 91.4 | 90.9 | 89.5 | — |
| 2% Propyl Gallate | 97.6 | 95.2 | 95.4 | 99.5 | 92.6 | 96.8 |
| 1% BHT; 1% EDTA | 96.5 | 92.8 | — | 91.0 | 90.0 | 89.2 |
| TFX Control | 98.0 | 93.6 | 83.8 | 82.0 | 67.5 | 58.9 |

[1]BHT = Butylated hydroxy-toluene

The above results illustrate the propyl gallate is the most efficient stabilizer for TFX technical.

EXAMPLE 4

Following the procedure as outlined in Example 3 above, additional additives were tested at 50° C. and 60° C. to determine their effectiveness as thermal stabilizers for TFX technical. In these studies, another batch of TFX technical (No. 2) was employed for most of the tests, while still another batch of technical (No. 1) was used with lesser quantities of propyl gallate than used with TFX No. 2. Samples of TFX technical materials without additives were similarly tested as controls. As followed in Example 3, the initial assay of each sample was considered as 100% TFX technical and the subsequent assays measured were calculated as percentages of the initial assays. The results are as follows:

TABLE 3

| | Percent TFX TECHNICAL Remaining | |
|---|---|---|
| | 50° C. | 60° C. |
| Sample | 8 weeks | 8 weeks–12 weeks |
| Additive TFX 2 | | |
| 2% Anthranilic Acid | 87.7 | 84.7 52.0 |
| 2% Tolyltriazole | 81.1 | 50.8 26.4 |
| 2% BHA | 83.2 | 71.8 48.9 |

TABLE 3-continued

| Sample | Percent TFX TECHNICAL Remaining | | |
|---|---|---|---|
| | 50° C. 8 weeks | 60° C. 8 weeks | 12 weeks |
| 2% Gallic Acid | 95.6 | 93.5 | 91.5 |
| 2% Erythorbic Acid | 94.0 | 92.6 | 92.8 |
| 2% Propyl Gallate | 95.0 | 94.4 | 92.6 |
| .5% Propyl Gallate; 5% EDTA | 96.4 | 95.7 | 94.9 |
| TFX 2 Control | 83.5 | 79.5 | 45.8 |
| TFX 1 + Additive | | | |
| 0.1% Propyl Gallate | 97.4 | 95.4 | 95.0 |
| 1.0% Propyl Gallate | 96.7 | 96.3 | 96.0 |
| TFX 1 Control | 92.0 | 88.8 | 87.8 |

The above results indicate that the thermal stability of TFX technical may vary substantially from batch to batch. Thus, it can easily be recognized that the stabilizing method according to this invention will be especially advantageous when employed with TFX technical material which inherently has a lower level of thermal stability.

EXAMPLE 5

The comparative thermal stability characteristics imparted to TFX technical by incorporating various concentrations of propyl gallate therein were determined, using the 25×20 ml. scintillation vials filled with the various TFX-propyl gallate mixtures prepared in Example 2 above.

Some samples were stored for 12 weeks at 20° C., others at 40° C., and those remaining at 60° C. The latter samples were assayed after being stored for 6 weeks and for 8 weeks at 60° C. The initial assays of all the samples were taken as 100 percent TFX technical, with the subsequent assays being calculated as percentages of the initial assays. The results obtained are as follows:

TABLE 4

| TFX Sample | Assays - % TFX TECHNICAL | | | | |
|---|---|---|---|---|---|
| | Weeks at 20° C. 12 | Weeks at 40° C. 12 | Weeks at 60° C. | | |
| | | | 6 | 8 | 12 |
| No Additive (1) | 98.4 | 96.1 | 62.1 | 50.5 | 56.7 |
| 0.05% Propyl Gallate | 96.0 | 95.0 | 89.8 | — | 86.1 |
| 0.10% Propyl Gallate | 97.8 | 96.5 | 101.0 | — | 94.9 |
| 0.50% Propyl Gallate | 96.9 | 96.9 | 96.1 | — | 94.4 |
| 1.0% Propyl Gallate | 100.7 | 99.0 | — | — | 96.6 |
| 2.0% Propyl Gallate | 97.6 | 97.2 | 96.4 | — | 93.5 |
| 2.0% EDTA Acid | 97.1 | 96.0 | 98.1 | 99.1 | 95.8 |
| No Additive (2) | 97.2 | 95.0 | 42.2 | 43.0 | 52.2 |

In these samples, the first TFX control was taken from the bottom of the drum, while the second TFX control was drawn from the top of the drum. The second control sample was not quite as stable as the first control sample, although it was the same batch of TFX. Being taken from the top of the drum, where less dense components of TFX technical would be more concentrated, the second control sample presumably contained more impurities.

What is claimed is:

1. A stabilized composition comprising an oxime carbamate of the formula:

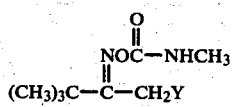

wherein Y is —SCH$_3$ or —N$_3$, in combination with gallic acid or a lower alkyl esters thereof as stabilizer for said oxime carbamate.

2. The composition of claim 1 wherein the lower alkyl ester of gallic acid employed is propyl gallate.

3. The composition of claim 1 wherein the amount of gallic acid or the propyl ester thereof is in the range of 0.05 to 2.0 percent, by weight of the oxime carbamate.

4. The composition of claim 1 wherein the amount of gallic acid or the propyl ester thereof is in the range of 0.1 to 1.0 percent, by weight of the oxime carbamate.

5. The composition of claim 1 wherein the oxime carbamate is 3,3-dimethyl-2-methylcarbamate oximino-1-methylthiobutane.

6. The composition of claim 1 wherein the oxime carbamate is 1-azido-3,3-dimethyl-2-methylcarbamyloximino-butane.

7. The composition of claim 1 which additionally contains a solid carrier for the oxime carbamate.

8. The composition of claim 7 wherein the oxime carbamate is 3,3-dimethyl-2-methylcarbamate oximino-1-methylthiobutane.

* * * * *